United States Patent [19]

Buultjens et al.

[11] Patent Number: 5,068,315
[45] Date of Patent: Nov. 26, 1991

[54] COMPOSITION FOR THE REGULATION OF HAIR GROWTH

[75] Inventors: Travis E. J. Buultjens, Dundee; Colin A. B. Jahoda; Roy F. Oliver, both of Fife, all of United Kingdom

[73] Assignee: University of Dundee, Scotland

[21] Appl. No.: 508,339

[22] Filed: Apr. 12, 1990

[51] Int. Cl.$^5$ .................... C07K 15/00; A61K 37/02
[52] U.S. Cl. .................................. 530/324; 530/300; 530/350; 530/842
[58] Field of Search ............... 530/324, 350, 300, 842; 514/880, 21; 424/401

[56] References Cited

U.S. PATENT DOCUMENTS

| | | | |
|---|---|---|---|
| 4,139,619 | 2/1979 | Chidsey | 424/45 |
| 4,670,255 | 6/1987 | Yoshizumi et al. | 424/93 |
| 4,832,946 | 5/1989 | Green | 424/70 |

FOREIGN PATENT DOCUMENTS

| | | |
|---|---|---|
| 221208 | 5/1987 | European Pat. Off. . |
| 225639 | 6/1987 | European Pat. Off. . |
| 335554 | 10/1989 | European Pat. Off. . |
| 352894 | 1/1990 | European Pat. Off. . |
| 0352984 | 1/1990 | European Pat. Off. . |
| 3431266 | 3/1986 | Fed. Rep. of Germany . |
| 2395756 | 6/1977 | France . |
| 63284-112A | 5/1987 | Japan . |
| 1563824 | 4/1980 | United Kingdom . |
| 2088210 | 6/1982 | United Kingdom . |
| 87/00201 | 1/1987 | World Int. Prop. O. . |

OTHER PUBLICATIONS

"The Developmental Appearance of a Major Basilar Papilla-Specific Protein in the Chick", Hearing Research, vol. 23, pp. 161-168 (1986).
"Binding Proteins for Sweet Compounds from Gustatory Papillae of the Cow, Pig and Rat", Biochimica et Biophysica Acta, vol. 967, pp. 65-75 (1988).
CA 110 (1) 5089k, 1988.
CA 105 (13) 112673g, 1986.
U.S. patent Appln. Ser. No. 525171-Buultjens et al., 5/22/90.
Sporn, M. B. and A. B. Roberts, (1988), "Peptide Growth Factors are Multifunctional", Nature vol. 332, pp. 217-219.
Horne, K. A. et al., (1986), "Hair-Growth-Promoting Properties of Dermal Papilla Cells in the Rat", Journal of Physiology (Lond), p. 48P.
Horne, K. A. et al. (1986), "Whisker Growth Induced by Implantation of Cultured Vibrissa Dermal Papilla Cells in the Adult Rat", Journal of Embryology and Experimental Morphology, vol. 97, pp. 111-124.
Withers, A. P. et al., (1986), "Culture of Wool Follicle Dermal Papilla Cells from Two Breeds of Sheep", Archives of Dermatological Research, vol. 279, pp. 140-142.
Jahoda, C. A. B. et al. (1984), "Vibrissa Dermal Papilla Cell Aggregative Behavior in vivo and in vitro", Journal of Embryology and Experimental Morphology, vol. 79, pp. 211-224.
Jahoda, C. A. B. et al., (1984), "Induction of Hair Growth by Implantation of Cultured Dermal Papilla Cells", Nature, vol. 311, pp. 560-562.
Messenger, A. G., (1984), "The Culture of Dermal Papilla Cells from Human Hair Follicles", British Journal of Dermatology, vol. 110, pp. 685-689.
Jahoda, C. A. B. et al., (1984), "Changes in Hair Growth Characteristics Following the Wounding of Vibrissa Follicles in the Hooded Rat", Journal of Embryology and Experimental Morphology, vol. 83, pp. 81-93.
Jahoda, C. et al., (1981), "The Growth of Vibrissa Dermal Papilla Cells in Vitro", British Journal of Dermatology, vol. 105, pp. 623-627.
Ibrahim, L. et al., (1977), "Inductive Capacity of Irradiated Dermal Papillae", Nature, vol. 265, pp. 733-734.
Oliver, R. F., (1970), "The Induction of Hair Follicle Formation in the Adult Hooded Rat by Vibrissa Dermal Papillae", Journal of Embryology and Experimental Morphology, vol. 23, pp. 219-236.
Oliver, R. F., (1967), "The Experimental Induction of Whisker Growth in the Hooded Rat by Implantation of Dermal Papillae", Journal of Embryology and Experimental Morphology, vol. 18, pp. 43-51.
Oliver, R. F., (1966), "Whisker Growth After Removal of the Dermal Papilla and Lengths of Follicle in the Hooded Rat", Journal of Embryology and Experimental Morphology, vol. 15, pp. 331-347.
Oliver, R. F., (1966), "Histological Studies of Whisker Regeneration in the Hooded Rat", Journal of Embryology and Experimental Morphology, vol. 16, pp. 231-244.
Cohen, J., (1961), "The Transplantation of Individual Rat and Guinea-Pig Whisker Papillae", Journal of Embryology and Experimental Morphology, vol. 9, pp. 117-127.

Primary Examiner—Thurman K. Page
Assistant Examiner—G. S. Kishore
Attorney, Agent, or Firm—Brahm J. Corstanje; Milton B. Graff, IV; Jerry J. Yetter

[57] ABSTRACT

Disclosed is a composition for regulating hair growth comprising a safe and effective amount of a polypeptide having the structure of those derived from dermal papilla cells with characteristics of apparent isoelectric pH/molecular weight selected from the group consisting of pI 5.1/45kD, pI 5.2/43kD, pI 5.2/40kD, pI 7.3/25kD, pI 7.4/25kD, or active fragment of these polypeptides, and mixtures thereof; and a pharmaceutically-acceptable carrier.

1 Claim, No Drawings

COMPOSITION FOR THE REGULATION OF HAIR GROWTH

TECHNICAL FIELD

The present invention relates to novel compositions which regulate hair growth.

BACKGROUND OF THE INVENTION

Society in general continues to attach a stigma to hair loss. The desire for a healthy full head of hair has resulted in a variety of approaches to the "curing" of baldness. Among the multitude of hair growth studies that have been reported in the literature, several researchers have directed their study to the hair bulb. The hair bulb is a compact, elongate structure, located in the dermis, composed of three main cellular groups. The first comprises a compact group of fibroblasts known as the dermal papilla which includes a capillary system. The second group comprises germinative epithelial cells of the hair bulb which proliferate and differentiate to give rise to the mature hair shaft. The third group of fibroblasts exists around the outside of the bulb in the connective tissue sheath.

The dermal papilla is present as an aggregation of mesenchymal cells throughout the development of hair follicles in the embryo. The importance of the dermal papilla in hair growth and follicle induction in the adult has been demonstrated in a series of studies on the rat vibrissa follicle (see Oliver, R. F. "Whisker Growth After Removal of the Dermal Papilla and Lengths of the Follicle in the Hooded Rat" 15 *Journal of Embryology and Experimental Morphology* 331 (1966a); Oliver, R. F. "Histological Studies of Whisker Regeneration in the Hooded Rat" 16 *Journal of Embryology and Experimental Morphology* 231 (1966b)). It has been shown that surgical removal of the vibrissa follicle dermal papilla leads to a cessation of hair growth (see Oliver 1966a; Oliver 1966b; Oliver, R. F. "The Experimental Induction of Whisker Growth in the Hooded Rat by Implantation of Dermal Papillae" 18 *Journal of Embryology and Experimental Morphology* 43 (1967)). Resumption of hair growth in such follicles occurs when a new dermal papilla is regenerated or a new dermal papilla is implanted into the ablated follicle. The role of the dermal papilla in de novo follicle induction has been established in a series of recombination experiments in which rat vibrissa dermal papillae were combined with either glabrous ear or afollicular scrotal sac epidermas resulting in the formation of vibrissa-type follicles in the respective epidermal sheets (see Oliver, R. F. "The Induction of Follicle Formation in the Adult Hooded Rat by Vibrissa Dermal Papilla" 23 *Journal of Embryology and Experimental Morphology* 219 (1970)). Dermal papillae from hair follicles of a variety of species can be explanted in Vitro and give rise to distinctive populations of cells with characteristic behavioral and morphological properties (see Jahoda, C.A.B. and R. F. Oliver "The Growth of Vibrissa Dermal Papilla Cells In Vitro" 105 *British Journal of Dermatology* 623 (1981); Jahoda, C.A.B. and R. F. Oliver "Vibrissa Dermal Papilla Cell Aggregative Behaviour In Vivo and In Vitro" 83 *Journal of Embryology and Experimental Morphology* 81 (1984); Messenger, A.G. "The Culture of Dermal Papilla Cells From Human Hair Follicles" 110 *British Journal of Dermatology* 685 (1984); Withers, A.P., C.A.B. Jahoda, M. L. Ryder and R. F. Oliver "Culture of Wool Follicle Dermal Papilla Cells From Two Breeds of Sheep" 279 *Arch. Dermatol. Res* 140 (1984)). A remarkable property of the cells cultured from the dermal papillae of adult rat vibrissa follicles is the retention of the capacity to induce hair growth when introduced into the follicle cavities formed by the amputation of the lower halves of the follicle. (See Jahoda, C.A.B., K. A. Horne and R. F. Oliver "Induction of Hair Growth by Implantation of Cultured Dermal Papilla Cells" 311 *Nature London* 560 (1984); Horne, K. A., C.A.B. Johoda and R. F. Oliver "Whisker Growth Induced by Implantation of Cultured Vibrissa Dermal Papilla Cells in the Adult Rat" 97 *Journal of Embryology and Experimental Morphology* 111 (1986)). It has also been demonstrated that cultured papilla cells are capable of restimulating the growth of hair when introduced into follicles which have been rendered inactive as well as inducing morphogenesis of completely new hair follicles and the subsequent production of hair fibres. (Horne, K. A., C.A.B. Jahoda, R. F. Oliver and A. J. Reynolds, "Hair-Growth-Promoting Properties of Dermal Papilla Cells in the Rat" 380 *Journal of Physiology* (London) 48P (1986)).

U.S. Pat. No. 4,832,946, Green, issued May 23, 1989, assigned to Unilever, discloses a composition for topical application to mammalian hair or skin, comprising an amount of the cell-free supernatant from a culture of dermal papilla fibroblasts which increases hair growth in the rat by at least 10% more than that of a control composition.

German Patent DE 3 431 266, Birzer, published Mar. 6, 1986, discloses that external or internal administration of hair bulb cells with the papilla from slaughtered animals stimulates growth and genesis of hair and counteracts hair loss and hair greying. The cells are obtained from the hide of animals and can be applied internally by injection or as tablets or drops, and externally as shampoos, creams and soaps.

PCT Patent Application No. WO 85/04577, Bazzano, published Oct. 24, 1985 discloses a composition containing a pyrimidine carbamate which increases the rate of hair growth on mammalian skin, prolongs the growth phase of the hair growth cycle, and treats various types of alopecias.

U.S. Pat. No. 4,139,619, Chidsey, issued Feb. 13, 1979, assigned to the Upjohn Company, discloses a topical composition comprising Minoxidil and related iminopyrmidines which stimulates the conversion of vellus hair to terminal hair and increases the rate of growth of terminal hair.

OBJECTS OF THE PRESENT INVENTION

It is an object of the present invention to provide a purified hair growth regulating polypeptide.

It is a further object of the present invention to provide a composition for regulating hair growth.

It is also an object of the present invention to provide a composition for regulating hair growth, which is suitable for topical application to mammalian skin or hair.

It is also an object of the present invention to provide a composition for regulating hair growth, which is suitable for application via cutaneous injection.

It is also an object of the present invention to provide a method of regulating hair growth, which comprises applying to mammalian skin or hair a topical composition.

It is also an object of the present invention to provide a method of regulating hair growth, which comprises cutaneous injection of a composition.

SUMMARY OF THE INVENTION

The present invention relates to a composition for regulating hair growth comprising a safe and effective amount of a polypeptide having the structure of those derived from dermal papilla cells with characteristics of apparent isoelectric pH/molecular weight selected from the group consisting of pI 5.1/45 kD, pI 5.2/43 kD, pI 5.2/40 kD, pI 7.3/25 kD, pI 7.4/25 kD, or active fragment of these polypeptides, and mixtures thereof; and a pharmaceutically-acceptable carrier.

DETAILED DESCRIPTION OF THE INVENTION

As used herein, "apparent isoelectric pH" means the isoelectric pH that is determined by the two-dimensional polyacrylimide gel electrophoresis procedures disclosed in O'Farrell, P.H., "High Resolution Two-dimensional Electrophoresis of Proteins", 250 *Journal of Biological Chemistry* 4007 (1975) and O'Farrell, P.H., "High Resolution Two-dimensional Electrophoresis of Basic as Well as Acidic Proteins", 12 *Cell* 1133 (1977). The specific procedure is disclosed in the Example below.

As used herein, "topical application" means directly laying on or spreading on outer skin or hair.

As used herein, "cutaneous injection" means introduction of a substance beneath or within the skin by a hypodermic needle.

As used herein "safe and effective amount" means a sufficient amount of a composition to provide a desired hair growth regulating effect at a reasonable benefit/risk ratio.

As used herein "pharmaceutically-acceptable" means that drugs, medicaments or inert ingredients which the term describes are suitable for use in contact with the tissues of humans and lower animals without undue toxicity, irritation, allergic response, and the like, commensurate with a reasonable benefit/risk ratio.

As used herein, "purified polypeptide" means a polypeptide sample having a more uniform composition and freer from adulterants, impurities, or contaminants than an intracellular extract or extracellular supernatant comprising the same polypeptide. A variety of mechanical, chemical and biological methods for purifying samples are available in the art. Such examples include, but are not limited to, gel electrophoresis, filtration, gradient centrifugation, crystalization, precipitation, ion exchange chromatography, lyophilization and dialysis.

As used herein, "regulating hair growth" means inducing the formation of a greater number of hair strands, and/or increasing the diameter of the hair strand, and/or lengthening the hair strand, and/or preventing, retarding, or arresting the process of hair loss.

As used herein, all percentages are by weight unless otherwise specified.

Hair Growth Regulating Polypeptides

The present invention involves a purified hair growth regulating polypeptide (hereinafter HGRP) having the structure of those derived from dermal papilla cells with characteristics of apparent isoelectric pH/molecular weight selected from the group consisting of pI 5.1/45 kD, pI 5.2/43 kD, pI 5.2/40 kD, pI 7.3/25 kD, pI 7.4/25 kD, or active fragment of these polypeptides, and mixtures thereof. The present invention additionally involves the following compositions:

A composition for regulating hair growth comprising a safe and effective amount of a polypeptide having the structure of that derived from dermal papilla cells with an isoelectric pH of pI 5.1 and a molecular weight of 45 kD and a pharmaceutically-acceptable carrier.

A composition for regulating hair growth comprising a safe and effective amount of a polypeptide having the structure of that derived from dermal papilla cells with an isoelectric pH of pI 5.2 and a molecular weight of 43 kD and a pharmaceutically-acceptable carrier.

A composition for regulating hair growth comprising a safe and effective amount of a polypeptide having the structure of that derived from dermal papilla cells with an isoelectric pH of pI 5.2 and a molecular weight of 40 kD and a pharmaceutically-acceptable carrier.

A composition for regulating hair growth comprising a safe and effective amount of a polypeptide having the structure of that derived from dermal papilla cells with an isoelectric pH of pI 7.3 and a molecular weight of 25 kD and a pharmaceutically-acceptable carrier.

A composition for regulating hair growth comprising a safe and effective amount of a polypeptide having the structure of that derived from dermal papilla cells with an isoelectric pH of pI 7.4 and a molecular weight of 25 kD and a pharmaceutically-acceptable carrier.

The purified HGRPs of the present invention have a purity preferably greater than 80%, more preferably greater than 95%, more preferably greater than 99%, and most preferably greater than 99.9%.

The purified HGRPs of the present invention can be obtained by culturing dermal papilla cells in nutrient medium followed by lysing of the cells. Non-equilibrium pH gradient electrophoresis (NEPHGE) and sodium dodecyl sulfate polyacrylamide gel electophoresis (SDS-PAGE) techniques are then executed upon the cell lysates to isolate the desired polypeptides. The isolated polypeptides are then eluted from the gel to obtain the purified HGRPs.

EXAMPLE

The following example is intended to illustrate the process for purification as applied to a particular sample. It is not intended to limit the invention.

Cell Culture

Mammalian dermal papilla cells are removed from the bulb regions of vibrissa follicles and explanted into culture dishes as described in Jahoda, C.A.B. and R. F. Oliver, "The Growth of Vibrissa Dermal Papilla Cells In Vitro", 105 *British Journal of Dermatology* 623 (1981); and Jahoda, C.A.B. and R. F. Oliver, "Vibrissa Dermal Papilla Cell Aggregative Behaviour In Vivo and In Vitro", 83 *Journal of Embryology and Experimental Morphology* 81 (1984). The cells are maintained in Eagle's minimal essential medium (EMEM; GIBCO Ltd., Paisley, Scotland) supplemented with 4 mM glutamine, 50 units/ml penicillin, 50 ug/ml streptomycin and 20% foetal bovine serum (Gibco Ltd., Paisley, Scotland).

Identification by Molecular Weight and ph Gradient

The mammalian dermal papilla cells are plated out at $2-4 \times 10^4$ cells per 35 mm plastic petri dish (Nunc or Sterilin) in growth medium as above and maintained at 37° C. in a water-saturated atmosphere of 5% $CO_2$/air. The culture is grown to confluence. The culture is maintained at confluence without a change of growth medium for 48 hr and then labelled for 18-20 hr with 150 uCi/ml of L-[$^{35}$S]-methionine (Amersham International, A Public Limited Company, Amersham, England) in EMEM containing 1/10 of the normal methionine concentration and supplemented with 1% dialysed foetal bovine serum and glutamine and penicillin/ streptomycin.

Two-dimensional polyacrylamide gel electrophoresis procedures are based on those disclosed in O'Farrell (1975) and O'Farrell (1977). Labelled cell lysates are obtained by the addition of 150 μl of lysis buffer (9.5M urea, 2% Nonionic Surfactant Nonidet P40 and 2% Ampholines, pH 3.5-10 to each 35 mm culture dish. The radioactivity incorporated into each sample is determined by trichloroacetic acid (TCA) precipitation of 5 μl aliquots followed by liquid scintillation counting. Samples containing $10^6$ disintegrations per minute are spun on a microcentrifuge for 2 min., layered on cylindrical polyacrylamide gels (3×95 mm) containing Ampholines pH 3.5-10 (Pharmacia LKB Biotechnology Inc., Milton Keynes, England). Non-equilibrium pH gradient electrophoresis (NEPHGE) is carried out for 1650 volt hours at room temperature. After electrophoresing, the cylindrical gels are equilibrated in SDS-sample buffer before analysis in the second dimension on 10% or 12% slab gels (140×145×0.8 mm) by sodium dodecyl sulphatepolyacrylamide gel electrophoresis (SDS-PAGE). On completion of electrophoresis in the second dimension, the slab gels are fixed, treated with a fluorographic enhancer (Amersham International, A Public Limited Company, Amersham, England), dried under vacuum and exposed for 5 days to Kodak XAR film at −70° C.

The pH gradient generated in the first dimension cylindrical gel is determined by dividing a control gel into 10 mm segments, extracting each segment in 2 ml of deionized water for 16 hr at room temperature and determining the pH of each extract. The apparent molecular weights of polypeptides resolved in the second dimension are obtained from a calibration curve generated by the use of low molecular marker proteins (Bio-Rad Ltd, Watford, England).

Elution of the Polypeptides

Polypeptides which are to be eluted and later incorporated into a composition of the present invention are isolated from a non-radioactive lysate. Two lysate separations are run concurrently. The samples from a radiolabelled cell lysate are run on one gel, and samples from a non-radiolabelled cell lysate are run on a second gel. All other conditions are the same i.e., sample size, gel size, gel percent, buffer solution, volt hours, temperature, etc.

Following separation of the polypeptides from a non-radioactive cell lysate by 2-dimensional polyacrylamide gel electrode phoresis the bands on the 2nd gel corresponding to apparent isoelectric pH/molecular weights of pI 5.1/45 kD, pI 5.2/43 kD, pI 5.2/40 kD, pI 7.3/25 kD, and pI 7.4/25 kD are identified by the radiolabeled bands on the 1st gel. These areas are excised from the gel using a razor. Each excised band is placed in a piece of dialysis tubing which also contains an appropriate buffer solution (1.5g Tris, 7.2g Glycine, 0.5g Lauryl Sulfate in 500 ml water). The dialysis tubing containing the polypeptide and buffer is placed in an electrophoresis chamber containing the same buffer solution as found in the dialysis tubing. The polypeptide is electroeluted into the buffer solution of the dialysis tubing.

The excised gel no longer containing the polypeptide is removed from the tubing. The polypeptide eluted into the buffer solution of the tubing can be concentrated and/or subjected to lyopholization for use with the appropriate carrier.

Polypeptide Fragments

A fragment of the isolated polypeptide(s) can be generated by cleaving the native polypeptide with proteases. A variety of enzymes may be employed in such a procedure, including but not limited to, cyanogen bromide., trypsin, chymotrypsin, and pepsin.

A fragment of the isolated polypeptide(s) may also be generated by in vitro synthesis of specific areas of the native polypeptide by standard techniques.

Hair Growth Regulating Compositions

Another aspect of the present invention involves compositions for regulating hair growth comprising a safe and effective amount of a polypeptide having the structure of those derived from dermal papilla cells with characteristics of apparent isoelectric pH/molecular weight selected from the group consisting of pI 5.1/45 kD, pI 5.2/43 kD, pI 5.2/40 kD, pI 7.3/25 kD, pI 7.4/25 kD, or active fragment of these polypeptides, and mixtures thereof; and a pharmaceutically-acceptable carrier. The amount of the HGRPs to be incorporated with a suitable carrier into compositions for hair growth regulatory use can vary widely. Preferred amounts of a purified polypeptide in such compositions are from about 0.01% to about 20%, more preferred are from about 0.1% to about 5% by weight.

The Carrier

The compositions of the present invention comprise a solid, semi-solid or liquid cosmetically and/or physiologically acceptable carrier to enable the HGRPs to be delivered to the desired target at an appropriate concentration. The carrier can itself be inert or it can possess physiological or pharmaceutical benefits of its own. The nature of the carrier will be dictated by the method chosen for administration of the composition. The method of administration of the HGRP composition may range from internal methods such as injection to external topical methods.

A preferred method of administration of the HGRPs is by cutaneous injection. The carrier for facilitation of such administration would preferably comprise water or a saline solution.

A more preferred method of administration of the HGRPs is by topical application. Topical application is preferably achieved with compositions in the forms of sprays, tonics, creams, lotions, shampoos, and the like.

Topical compositions of the present invention can be formulated as liquids, for example as a lotion, cream, shampoo, conditioner or milk. Such liquid compositions may be formulated for use in conjunction with an applicator such as a roll-ball applicator, or a spray device such as an aerosol can containing propellant, or a container fitted with a pump to dispense the liquid product.

Alternatively, the compositions of the invention can be solid or semi-solid, for example sticks, creams or gels. Such solid or semi-solid compositions may be formulated for use in conjunction with a suitable applicator or simply a tube, or bottle, or as a liquid-impregnated fabric, such as a tissue wipe.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for the HGRPs which therefore ensure that it can be applied to and distributed evenly over the selected target at an appropriate concentration. The carrier is preferably one which can aid penetration -of the HGRPs into the skin to reach the immediate environment of the hair follicle. Topical carriers useful in compositions of the subject invention can include water as a vehicle, and/or at least one cosmetically acceptable vehicle other than water. Carriers useful in topical compositions according to the invention may include liposomes, latex latices, microphages, and various forms of microencapsulation of the HGRPs.

Generally, the carrier is either organic in nature or an aqueous emulsion and capable of having the HGRPs dispersed or dissolved therein. The carrier may include pharmaceutically-acceptable emollients, skin penetration enhancers, coloring agents, fragrances, emulsifiers, thickening agents, and solvents.

A more detailed description of preferred topical compositions follows:

1. Lotions

The lotions can comprise an effective amount (preferably from about 0.01% to about 10%, more preferably from about 0.1% to about 1%) of the HGRPs; from 1% to 50%, preferably from 3% to 15%, of an emollient; the balance being water, a $C_2$ or $C_3$ alcohol, or a mixture of water and the alcohol. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methylphenylpolysiloxanes, water-soluble and alcohol-soluble siliconeglycol copolymers and volitile silicone fluids such as cyclomethicane.

c. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monostearate.

f. Alkyl esters of fatty acids having 10 to 20 carbon atoms. Methyl, isopropyl and butyl esters of fatty acids are useful herein Examples include hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include oleyl myristate, oleyl stearate, and oleyl oleate.

h. Fatty acids having 8 to 22 carbon atoms Suitable examples include pelargonic, lauric, myristic, palmitic, stearic, isostearic, hydroxystearic, oleic, linoleic, ricinoleic, arachidonic, behenic, and erucic acids.

i. Fatty alcohols having 8 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j Fatty alcohol ethers. Ethoxylated fatty alcohols of 8 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

k. Ether-esters such as fatty acid esters of ethoxylated fatty alcohols.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

m. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly(ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivates of trimethylolpropane are examples thereof.

n. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbitol beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters are examples thereof.

t. Amides such as fatty acid amides, ethoxylated fatty ac&d amides, solid fatty acid alkanolamides.

The lotions further preferably comprise from 1% to 10%, more preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Curtain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams comprise an effective amount (preferably from about 0.01% to about 10%, more preferably from about 1% to about 5%) of the HGRPs; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The solution form comprises an effective amount (preferably from about 0.01% to about 10%, more preferably from about 0.1% to about 1%, of the HGRPs; the balance being water and/or a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellapt gases. These propellants are used at a level sufficient to expel the contents of the container.

4. Gels

Gel compositions can be formulated by simply admixing a suitable thickening agent to the previously described solution compositions. Examples of suitable thickening agents have been previously described with respect to the lotions.

The gel compositions comprise an effective amount (preferably from about 0.01% to about 10%, more preferably from about 1% to about 5%) of the HGRPs; from 5% to 75%, preferably from 10% to 50%, of an organic solvent as previously described; from 0.5% to 20%, preferably from 1% to 10% of the thickening agent; the balance being water.

5. Solids

Compositions of solid forms have use as stick-type compositions intended for application to the scalp or other parts of the body. Such compositions comprise an effective amount (preferably from about 0.01% to about 10%, more preferably from about 1% to about 5%) of the HGRPs, and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Penetration Enhancers

The presence of a penetration enhancer can potentiate the benefit of the HGRPs by improving their delivery through the stratum corneum to its site of action in the immediate environment of the hair follicle proximate to the dermal papilla.

The penetration enhancer can accordingly function in a variety of ways. It can, for example, improve the distribution of the hair growth promoter on the skin surface. Alternatively, it can increase its partition into the skin from the composition when applied topically, so aiding its passage to its site of action. Other mechanisms enhancing the benefit of the HGRPs may also be involved.

Examples of penetration enhancers include, but are not limited to: 1-dodecylazacycloheptan-2-one in combination with certain $C_3$–$C_4$ diols or a 1-substituted azacycloalkyl-2-one (see U.S. Pat. No. 4,557,934, Cooper, issued Dec. 10, 1985); a binary combination of a $C_3$–$C_4$ diol and a "cell-envelope disordering compound" (see U.S. Pat. No. 4,552,872, Cooper, Loomans and Fawzi, issued Nov. 12, 1985); a binary combination of N-(2-hydroxyethyl) pyrolidone and a "cell-envelope disordering compound" (see U.S. Pat. No. 4,537,776, Cooper, issued Aug. 27, 1985); a compound comprising lauryl alcohol, diisopropyl sebacate, dibutyl sebacate., dioctyl adipate, propylene glycol dipelargonate, butyl laurate, ethyl myristate, butyl myristate, isopropyl palmitate, oleyl alcohol, diethyl sebacate, dioctyl sabacate, dioctyl azelate, hexyl laurate, ethyl caprate, butyl stearate, isopropyl isostearate, 2-ethylhexyl pelargonate, butyl benzoate, benzyl benzoate, benzyl salicylate, dibutyl phthalate and/or ethyl laurate (see U.S. Pat. No. 4,299,826, Luedders, issued Nov. 10, 1981); a sugar ester in combination with a sulfoxide or phosphine oxide (see U.S. Pat. No. 4,150,114, Smith, issued Apr. 17, 1979; U.S. Pat. No. 4,148,917, Smith, issued Apr. 10, 1979;

U.S. Pat. No. 4,148,887, Smith, issued Apr. 10, 1979; U.S. Pat. No. 4,148,874 Smith, issued Apr. 10, 1979; U.S. Pat. No. 4,148,893, Smith, issued Apr. 10, 1979; U.S. Pat. No. 4,130,667, Smith, Dec. 19, 1978; U.S. Pat. No. 4,130,643, Smith, issued Dec. 19, 1978; U.S. 4,046,886, Smith, issued Sept. 6, 1977; U.S. Pat. No. 3,952,099, Smith, issued Apr. 20, 1976; U.S. Pat. No. 3,952,099, Smith, issued Apr. 20, 1976; U.S. Pat. No. 3,896,238, Smith, issued July 22, 1975); a carrier comprising alaphatic sulfoxides (See U.S. Pat. No. 3,953,599, MacMillan and Lyness, issued Apr. 27, 1976; U.S. Pat. No. 3,903,256, MacMillan and Lyness, issued Sept. 2, 1975; U.S. Pat. No. 3,839,566, MacMillan and Lyness, issued Oct. 1, 1974; U.S. Pat. No. 3,678,156, MacMillan and Lyness, issued July 18, 1972); a carrier comprising a binary combination of a $C_3$-$C_4$ diol or $C_3$-$C_6$ triol and a specific $C_{16}$ or $C_{18}$ alcohol polar lipid compound (See European Patent Application 249 397, Kasting, Smith, Massaro and Snyder, published Dec. 16, 1987); a carrier comprising a $C_3$-$C_4$ diol, diol ester or diol ether and a cell-envelope disordering compound (See European Patent Application 095 813, Cooper, published Dec. 7, 1983; European Patent Application 043 738, Wickett, Cooper and Loomans, published January 13, 1982); a carrier comprising a $C_6$-$C_{14}$ primary alkanol and a propane or butane diol (See European Patent Application 013 459, Wickett, Cooper and Loomans, published July 23, 1980);

Other Hair Growth Stimulants

The composition according to the invention can also optionally comprise pther hair growth stimulants capable of functioning in different ways to enhance the benefit of the HGRPs. Examples of other substances which themselves possess the ability to regulate hair growth include, but are not limited to, minoxidil, retinoic acid, diazoxide, iamin and its copper derivatives, anti-inflammatories, calcium channel blockers, anti-bacterials, non-ionic surfactants, mucopolysaccharides, and antiandrogens.

Other Ingredients

The composition according to the invention can contain ingredients other than those already mentioned, depending on the form of the intended product. It is, for example, possible to include antiseptics, preservatives, antioxidants, emulsifiers, coloring agents, soaps and detergents.

The composition according to the invention can also be employed as a vehicle for a wide variety of cosmetically or pharmaceutically active ingredients, particularly ingredients which have some beneficial effect when applied to the skin other than the promotion of hair growth.

The composition according to the invention can also optionally comprise a perfume in an amount sufficient to make the composition acceptable to the consumer and pleasant to use. Usually, the perfume will form from 0.01% to 0.1% by weight of the composition.

Use of Compositions to Induce, Maintain or Increase Hair Growth

The invention also provides for the use of the HGRPs isolated from cultured dermal papilla cells in the treatment of baldness. The following methods of use may be used to reverse, arrest, or prevent the onset of baldness.

The compositions according to the invention are preferably intended for application by cutaneous -injection. The amount of the composition and the frequency of cutaneous injection can vary widely, depending on personal needs. As an example of application by cutaneous injection, it is suggested that a composition suit able for cutaneous injection comprising the HGRPs be cutaneously injected preferably from once per day to once every six months, more preferably from three times per week to once per month, and most preferably from once per week to twice per month. The composition for cutaneous injection will preferably contain from about 0.001% to about 10% of the HGRPs, more preferably from about 0.01% to about 10%, and most preferably from about 0.1% to about 1%. The period of injections would preferably be over a period of from about one month to about ten years, more preferably from about three months to about two years, more preferably still from about six months to about one year, thereby resulting in regulation of hair growth.

A more preferred method of applying the compositions according to the present invention involves topical application to the scalp of a human subject to regulate hair growth, particularly where the head is already bald or balding. The amount of the composition and the frequency of application to the hair and/or scalp can vary widely, depending on personal needs, but it is suggested as an example that topical application preferably range from 8 to 10 times daily, more preferably from 4 to 6 times daily, more preferably from 2 to 3 times daily, and most preferably once per day. The composition for topical application will preferably contain from about 0.001% to about 10% of the HGRPs, more preferably from about 0.01% to about 10%, and most preferably from about 0.1% to about 1%. The period of topical application would preferably be over a period of from about one month to about ten years, more preferably from about three months to about two years, more preferably still from about six months to about one year, thereby resulting in regulation of hair growth.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. Polypeptides isolated from dermal papilla cells with characteristics of apparent isoelectric pH and molecular weight selected from the group consisting of pI 5.1 and 45 kD; pI 5.2 and 43 kD; pI 5.2 and 40 kD; pI 7.3 and 25 kD; and pI 7.4 and 25 kD.

* * * * *